United States Patent [19]

Huggler

[11] 4,129,903
[45] Dec. 19, 1978

[54] HINGE PROSTHETIC JOINT WITH BALL HEAD

[76] Inventor: Arnold H. Huggler, Steigstrasse 181a, Maienfeld, Switzerland

[21] Appl. No.: 802,144

[22] Filed: May 31, 1977

[30] Foreign Application Priority Data

Jun. 3, 1976 [CH] Switzerland .................. 7065/76

[51] Int. Cl.² ............................................. A61F 1/24
[52] U.S. Cl. ................. 3/1.913; 128/92 BB; 3/1.91
[58] Field of Search ............... 3/1.913, 1.912, 1.91; 128/92 C, 92 CA, 92 BA, 92 BB

[56] References Cited

U.S. PATENT DOCUMENTS

| | | | |
|---|---|---|---|
| 2,612,159 | 9/1952 | Collison | 128/92 BB |
| 2,682,265 | 6/1954 | Collison | 128/92 CA |
| 3,489,143 | 1/1970 | Holloran | 3/1.913 X |
| 3,987,499 | 10/1976 | Scharbach et al. | 3/1.913 X |

FOREIGN PATENT DOCUMENTS 2305333  8/1974  Fed. Rep. of Germany ............ 3/1.912

Primary Examiner—Ronald L. Frinks
Attorney, Agent, or Firm—Ladas, Parry, Von Gehr, Goldsmith & Deschamps

[57] ABSTRACT

A hinge prosthetic joint with a ball head, especially an endoprosthetic joint having a ball head for use with the proximal region of a bone such as the femur, wherein the ball head is provided with a traction or tension device for the anchoring thereof at an end of the bone. The tension device comprises a tension or tie rod which can be inserted through the bone, a pressure disc which can be placed into contact with the bone at the side of the ball head, and a counter plate which can be placed into contact with the opposite side of the bone.

13 Claims, 2 Drawing Figures

HINGE PROSTHETIC JOINT WITH BALL HEAD

BACKGROUND OF THE INVENTION

The present invention generally relates to the art of prosthetics, and more particularly concerns a hinge prosthetic joint having a ball head or ball, and especially an endoprosthetic joint having a ball head for use in conjunction with the proximal region or end of a bone, especially the femur.

With the heretofore known hinge prosthetic joints employing a ball head the latter is typically fixedly connected by an elongate anchor, or in fact forms an integrated part of the anchor, which is anchored internally of the tubular bone, for instance by means of cement.

Yet, it has been found that this solution is incapable of always fulfilling the prevailing requirements, especially in the presence of increased loads, where there repeatedly occur damage to the prosthetic joint or the bone.

SUMMARY OF THE INVENTION

Hence, it is a primary object of the present invention to provide a new and improved construction of prosthetic joint which overcomes the aforementioned drawbacks of the prior art constructions. Another and more specific object of the present invention aims at the provision of a new and improved construction of a hinge prosthetic joint having a ball head or ball, which is durable, sturdy, capable of resisting damage thereto or damaging the bone during normal usage.

Still a further significant object of the present invention aims at an improved prosthetic joint which is relatively simple in construction and design, economical to manufacture, easy to use, can be securely seated into the supporting bone and successfully resist forces tending to twist or dislodge it from its seat.

Now in order to implement these and still further objects of the invention, which will become more readily apparent as the description proceeds, the hinge prosthetic joint of the present development is manifested by the features that the ball or ball head is equipped with a tension or traction device for anchoring such ball head at an end of the related bone with which it is used. The tension device comprises a tension or tie rod which is insertable through the bone, a pressure disc which can be placed into contact with the bone at the side of the ball head, and a counter plate which can be placed into contact with the opposite side of the bone.

According to further features of the invention the end face or surface of the pressure disc confronting the bone is provided with a ring-shaped or annular groove which is intended to be placed over a resected bone neck end, in order to provide for the transverse stability of the pressure disc and the requisite resistance against twisting or torsion between the disc and the bone.

The ball head or ball can bear against the pressure disc by means of a sleeve-shaped pin or mandrel. The tension or tie rod is fixedly screwed internally of the pin or mandrel by means of a nut member or equivalent structure, and between the nut member and the floor or base of the sleeve-shaped pin there is arranged a compression spring, for instance a plate spring or a set of plate springs, so that the tension device is under a pre-bias or stress at all times and thus there is prevented any raising of the pressure disc from the bone when exposed to load.

Furthermore, means can be provided in order to secure the pressure disc, when assembled, against torsion or twisting. For instance, a safety and control screw arranged between the pressure disc and the counter plate above or parallel to the tension rod constitutes one such preferred form of means, and such screw simultaneously forms an additional tension or tie rod.

It is advantageous to provide the ball head or ball at a hollow pin or mandrel, the shaft of which surrounds the tension rod throughout the major portion of its length. Into the shaft of the hollow pin or mandrel there can be threaded at the head-end the tension rod. The shaft of the mandrel possesses a shoulder below the ball head or ball, and the surface of such shoulder which confronts the pressure disc is spherically domed or arched and cooperates with an appropriately formed seat provided in a central opening of the pressure disc.

When the prosthetic joint with a ball head or ball is designed as an endoprosthetic joint for the proximal region of the femur the pressure disc bears against the resected femur neck. The tension rod between the ball head support, also referred to as the pin or mandrel, and the counter plate secured to the lateral cortical layer of the tubular bone below the greater trochanter ensure that the pressure disc does not lift-off from the resected femur neck.

A characteristic aspect of the prosthesis of the invention is that the mechanical forces between the endoprosthetic joint and the femur are directly transmitted into the cortical layer of the femur, and therefore there is prevented any impermissible mechanical loading of the spongy structured bone lacunae (spongiosa).

Since the implantation of the hinge prosthetic joint of the invention only requires a minimum amount of bone cement there is extensively eliminated the danger of bone necrosis due to mechanical and chemical interaction between the bone tissue and cement. Further, due to the possibility of sufficiently resectioning the femur neck the invention enables counteracting the danger of bone necrosis of the neck extremety which anyway is poorly fed with blood.

A further advantage of the invention resides in the fact that the bone can be mechanically loaded at the direct region of the prothesis in the same manner as in the normal or intact physiological condition, and thus, as concerns so-called stress protection the bone therefore behaves completely normally.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
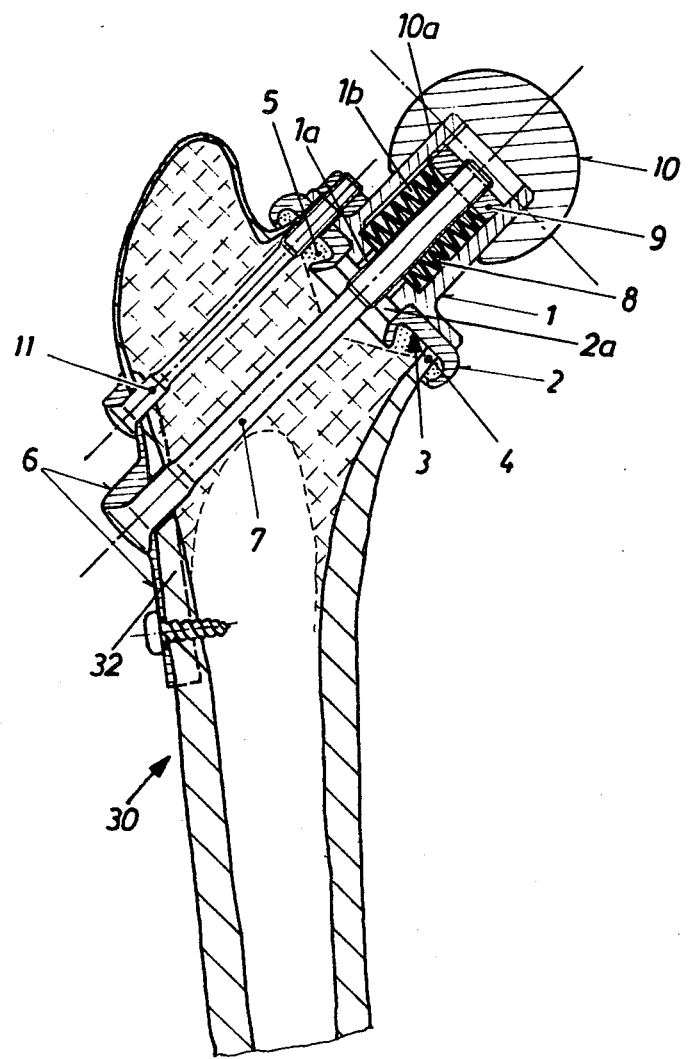
FIG. 1 is a sectional view through a prosthetic joint constructed as an endoprosthetic joint for the femur according to the invention.

Describing now the drawings, in FIG. 1 there is illustrated an exemplary embodiment of a prosthetic joint, here shown as an endoprosthetic joint for a femur bone and such joint being under continual stress or pre-bias. It will be recognized that a central sleeve-shaped pin or mandrel 1 together with a specially formed pressure disc 2 forms a unit or assembly. The pressure disc 2 contains a central recess and additionally possesses at its end face or surface confronting the bone 20, in this case the femur, a substantially ring-shaped or annular groove 3 serving as a seat for the end surface of the cortical layer of the resected femur neck 4. This ring-shaped groove 3 is filled with bone cement 5 before the assembly is finally inserted over the femur neck 4, so that there is ensured for a transverse stabilization of the implant as well as the requisite resistance against twisting or torsion between the pressure disc 2 and the bone 30.

An apertured or perforated plate 6 is mounted at the femur shaft 32 at the upper region of the M. Vastus lateralis, directly below the greater trochanter, so that a tension or tie rod 7 can be guided through such plate 6 and through a bore 1a provided in the pin or mandrel 1. At the proximal end of the sleeve-shaped pin or mandrel 1 there is located an enlarged bore 1b which houses a set of plate springs 8 or equivalent structure. A nut or nut member 9 which is threaded on to the tension or tie rod 7 exerts a force upon the set of plate springs 8 and produces the desired pre-bias or stress.

A ball 10 defining the ball head is equipped with a central bore 10a and forms the closure at the proximal end of the pin or mandrel 1.

Since the axis of the tension rod 7 is located above the center of gravity of the surface of the cross-section of the femur neck, greater pressure stresses appear in the upper portion of the femur neck than in the thicker lower portion. In the loaded condition there is extensively reduced the pressure stresses at the upper portion due to bending, whereas the pressure stresses increase in the lower portion. Under the condition that there prevails adequate pre-bias or stress, there need not be feared any lifting-off (i.e., complete reduction of the pressure stress) itself in the upper portion.

Nonetheless there is utilized to advantage an additional screw 11 or equivalent structure, arranged above the pre-biased tension rod 7, and serving as a safety and control element, for the event that unexpected forces might arise which could lead to undesired lifting of the prothesis from the femur neck. This screw 11 is also useful during radiography or the X-ray checking or control as an indicator for any possible recession of the pre-biased or stressed bone.

By means of simple surgery it is possible to tighten at any time both of the screws 7 and 11, in order to be able to re-establish completely the requisite pre-bias or stress.

Figure 2:
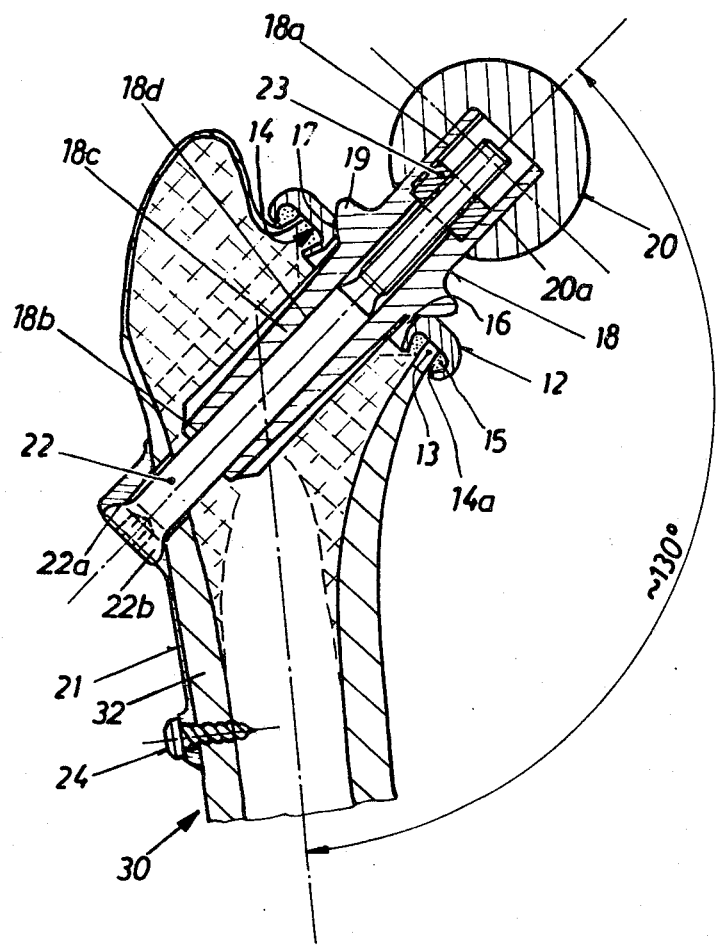
FIG. 2 is a variant embodiment of the prosthetic joint shown in FIG. 1, likewise illustrated in sectional view.

Continuing, and turning attention to the modified embodiment of prosthetic joint shown in FIG. 2 there is illustrated therein a femur-endoprosthetic joint having a flexible or bendable shaft. Following resectioning of the femur neck 13 there is mounted a specially formed pressure disc 12 at the end surface of such femur neck 13. Part of the resectioned neck enters a substantially ring-shaped or angular groove 14 at the side of the pressure disc 12 which confronts the bone 30, specifically the femur neck 13. The intermediate space 14a within the ring-shaped groove 14 is filled with bone cement 15, so that there cannot arise any transverse shifting or displacement between the pressure disc 12 and the bone 30. Furthermore, this cement layer provides the necessary resistance towards torsion or twisting. At the center of the pressure disc 12 there is provided a central opening or bore 16 which transforms at the outside region thereof into a substantially spherical seating surface or seat 17.

A pin or mandrel 18 having an appropriate spherical shoulder 19 is seated within the pressure disc 12, the shoulder 19 bearing against the seat or seating surface 17. The proximal end 18a of the pin or mandrel 18 is constructed such that a ball or ball head 20 having an appropriate bore 20a can be seated thereon. The end 18b of the shaft 18c of the pin or mandrel 18, and which end is located interior of the bone 30, extends quite close to the lateral cortical layer. The axis of the pin or mandrel 18 forms an angle of about 130° with the lengthwise axis of the femur 30.

At the outside, at the lateral outer or jacket surface of the femur 30, below the greater trochanter, there is arranged a counter plate 21. A screw 22 (tension or tie rod) possessing a spherical contact surface 22a at its head 22b penetrates through the substantially bracket-shaped counter plate 21 and the cortical layer located therebelow. This screw or tension rod 22 is guided through a bore 18d in the pin or mandrel 18 in such a manner that a nut or nut member 23 can be threaded at the proximal end 18a of the pin or mandrel 18. The nut 23 is countersunk within the pin or mandrel 18. The plate 21 is secured by a number of bone pins or screws 24 at the thick cortical at the region of the M. Vastus lateralis.

In the unloaded or rest position, that is to say, when no forces act upon the ball head or ball 20 then the pressure disc 12 is located at the femur neck and the plate 21 below the greater trochanter at most is in a slightly pre-biased condition, which is brought about by the pre-biasing action exerted by the screw 22. There is possibly also present a pre-bias or stress at the region of the plate 21, i.e., in the thick lateral cortical layer, which is brought about by the action of the screws 24.

Under load the pin or mandrel 18 is pressed by the action of the normal force components against the pressure disc 12 and the femur neck takes-up such pressure force, just as in the physiologically intact condition. The transverse force components acting upon the ball head or ball 20 cause a bending at the region of the pressure disc and is also still present as a transverse force at the pressure disc 12. The thus produced bending should be maintained away from the pressure disc-femur neck-connection as much as possible, since a bending to the full extent certainly will lead to a lifting-off of the pressure disc at the upper region of the femur neck. In order to counteract such, and while taking into account the elasticity of the bone, there is provided as good as possible bending-resistant connection between the pin or mandrel 18 and the lateral cortical layer below the greater trochanter. This is accomplished by means of the shaft screw 22 and the plate 21. Owing to the requisite bending-resistance it is therefore necessary for the screw 22 to fit with as little play as possible into the bore 18d of the pin or mandrel 18. The spherical seating surfaces or seats between the mandrel 18 and the pressure disc 12 as well as also between the screw 22 and the plate 21 facilitate the assembly and allow for slight geometric deviations during the resecting of the femur neck.

Here also a further screw could be threaded above the bending-resistant shaft 18c of the pin 18 and serve as an additional safeguard against any lifting-off of the pressure disc 12 from the femur neck.

Also with this solution, if necessary, the screw or screws can be tightened at any time by simple surgical techniques.

In either construction, the pressure disc may be so formed that the surface bearing on the bone is formed of ceramic material.

While there are shown and described present preferred embodiments of the invention, it is to be distinctly understood that the invention is not limited thereto, but may be otherwise variously embodied and practiced within the scope of the following claims. Accordingly,

What is claimed is:

1. A hinge prosthetic joint for a bone, especially a proximal femur-endoprosthetic joint, comprising:
    a ball;
    a tension device for anchoring the ball at an end of the bone where the prosthetic joint is implanted, said tension device comprising a tension rod insertable through the bone, a pressure disc which can be placed upon the bone at the side of the ball, and a counter plate which can be placed at the opposite side of the bone;
    a substantially sleeve-shaped hollow pin for mounting the ball at the pressure disc, said tension rod extending into the hollow interior of said sleeve-shaped pin; and
    a nut member for threadably connecting said tension rod within said sleeve-shaped pin.

2. The prosthetic joint as defined in claim 1, wherein:
    said pressure disc has an end surface confronting the bone and equipped with a substantially ring-shaped groove enabling the pressure disc to be placed over a resected end of the bone neck, in order to provide the transverse stability of the pressure disc and the requisite resistance against twisting between the pressure disc and the bone.

3. The prosthetic joint as defined in claim 1, further including:
    means provided for the counter plate for connecting the counter plate with the cortical layer of the bone in the implanted condition of the prosthetic joint.

4. The prosthetic joint as defined in claim 1, wherein:
    said pressure disc has a surface bearing at the bone; and
    at least said surface of said pressure disc being formed of ceramic material.

5. The prosthetic joint as defined in claim 1, wherein:
    said sleeve-shaped pin includes a base portion;
    a compression spring arranged between said nut member and said base portion of said sleeve-shaped pin, so that said tension device is subjected to prebias at all times and thus prevents lifting-off of the pressure disc from the bone under load.

6. The prosthetic joint as defined in claim 5, wherein: said compression spring comprises at least one plate spring.

7. The prosthetic joint as defined in claim 5, wherein:
    said compression spring comprises a set of plate springs.

8. The prosthetic joint as defined in claim 1, further including:
    a safety- and control screw means arranged between the counter plate and the pressure disc above the tension rod, so that when the prosthetic joint is implanted there is avoided under load any lifting-off of the pressure disc from the bone.

9. A hinge prosthetic joint for a bone, especially a proximal femur-endoprosthetic joint, comprising:
    a ball;
    a hollow pin at which the ball is provided, said hollow pin having a shaft provided with a shoulder below the ball, said shoulder being substantially spherically curved at its surface remote from the ball;
    a tension device for anchoring the ball at an end of the bone where the prosthetic joint is implanted, said tension device comprising a tension rod insertable through the bone and surrounded over the major portion of its length by said pin shaft, and the tension rod having a head-end and being threadably connected from the side of its head-end into the pin shaft, and the tension device further comprising a pressure disc which can be placed upon the bone between the bone and the shoulder of the pin shaft and has a central opening equipped with means defining a seat which coacts with the spherically curved surface of said shoulder, and
    a counter plate which can be placed at the side of the bone remote from said pressure disc.

10. The prosthetic joint as defined in claim 9, further including:
    means for securing the pressure disc against rotation in the implanted condition of the prosthetic joint.

11. The prosthetic joint as defined in claim 9, wherein said pressure disc has an end surface confronting the bone and equipped with a substantially ring-shaped groove enabling the pressure disc to be placed over a resected end of the bone neck, in order to provide the transverse stability of the pressure disc and the requisite resistance against twisting between the pressure disc and the bone.

12. The prosthetic joint as defined in claim 9, further including means provided for the counter plate for connecting the counter plate with the cortical layer of the bone in the implanted condition of the prosthetic joint.

13. The prosthetic joint as defined in claim 9, wherein said pressure disc has a surface bearing at the bone, and at least said surface of said pressure disc is formed of ceramic material.

* * * * *